United States Patent
Appiah-Amponsah et al.

(10) Patent No.: US 9,995,723 B2
(45) Date of Patent: Jun. 12, 2018

(54) METHOD FOR MEASURING FORMALDEHYDE IN SOLUTIONS CONTAINING CERTAIN FORMALDEHYDE-RELEASING BIOCIDES

(71) Applicant: Dow Global Technologies LLC, Midland, MI (US)

(72) Inventors: Emmanuel Appiah-Amponsah, Royersford, PA (US); Diamond Dyer, Collegeville, PA (US); Kelcie Zegalia, Collegeville, PA (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 203 days.

(21) Appl. No.: 15/234,011

(22) Filed: Aug. 11, 2016

(65) Prior Publication Data

US 2017/0052155 A1 Feb. 23, 2017

Related U.S. Application Data

(60) Provisional application No. 62/206,400, filed on Aug. 18, 2015.

(51) Int. Cl.
*G01N 30/88* (2006.01)
*G01N 33/18* (2006.01)
*G01N 30/74* (2006.01)

(52) U.S. Cl.
CPC ............ *G01N 33/18* (2013.01); *G01N 30/88* (2013.01); *G01N 30/74* (2013.01); *G01N 2030/884* (2013.01)

(58) Field of Classification Search
None
See application file for complete search history.

(56) References Cited

PUBLICATIONS

Fekete, et al., "Development of a capillary electrophoresismass spectrometry method for the determination of formaldehyde releasers as their hydrolysis products and amino alcohols from metal working fluids", Electrophoresis, vol. 27, pp. 2216-2224 (2006).

*Primary Examiner* — Paul S Hyun
(74) *Attorney, Agent, or Firm* — Kenneth Crimaldi

(57) ABSTRACT

A method for measuring formaldehyde in an aqueous solution of an oxazolidine or hexahydro-1,3,5-triazine biocide; the method comprising separating an amino alcohol produced by hydrolysis of the biocide via mixed mode chromatography and detecting the amino alcohol using a charged aerosol detector or an evaporative light scattering detector.

7 Claims, No Drawings

METHOD FOR MEASURING FORMALDEHYDE IN SOLUTIONS CONTAINING CERTAIN FORMALDEHYDE-RELEASING BIOCIDES

BACKGROUND

This invention relates generally to a method for determining formaldehyde content of aqueous solutions containing oxazolidine or hexahydro-1,3,5-triazine biocides.

The ability to accurately determine levels of "free" formaldehyde in solutions of formaldehyde-releasing biocides is critical to evaluating performance and risks associated with these biocides. Current methods for determining formaldehyde levels in these compounds typically result in exaggerated levels of formaldehyde due to hydrolysis of the biocide to produce formaldehyde during analysis. Hydrolysis can occur during chemical derivatization of formaldehyde or during the separation of formaldehyde or its derivative from other components, see for example, A. Fekete et al., *Electrophoresis*, 2006, vol. 27, pp. 2216-2224.

STATEMENT OF INVENTION

The present invention is directed to a method for measuring formaldehyde in an aqueous solution of an oxazolidine or hexahydro-1,3,5-triazine biocide; said method comprising separating an amino alcohol produced by hydrolysis of said biocide via mixed mode chromatography and detecting said amino alcohol using a charged aerosol detector or an evaporative light scattering detector.

DETAILED DESCRIPTION

All percentages are weight percentages (wt %), and all temperatures are in ° C., unless otherwise indicated. Unless otherwise specified, all operations were performed at room temperature (20-25° C.). As used herein the term "oxazolidine or hexahydro-1,3,5-triazine biocides" refers to compounds having microbiocidal activity and having an oxazolidine or a hexahydro-1,3,5-triazine ring which produces formaldehyde upon hydrolysis. Preferred oxazolidine biocides include, e.g., 4,4-dimethyloxazolidine (DMO), 5-ethyl-3,7-dioxa-1-azabicyclo[3,3,0]octane (EDAO) and N,N-methylenebis(5-methyloxazolidine). Preferred hexahydro-1,3,5-triazine biocides include, e.g., N,N,N-tris(2-hydroxyethyl)hexahydrotriazine and N,N,N-tris(2-hydroxypropyl)hexahydrotriazine.

Preferably, the oxazolidine or hexahydro-1,3,5-triazine biocide is an oxazolidine biocide, preferably one having a molecular weight no greater than 500, preferably no greater than 400, preferably no greater than 300, preferably no greater than 200. Preferably, the oxazolidine biocide is 4,4-dimethyloxazolidine (DMO), 5-ethyl-3,7-dioxa-1-azabicyclo[3,3,0]octane (EDAO) or N,N-methylenebis(5-methyloxazolidine).

Some oxazolidine and hexahydro-1,3,5-triazine biocides are known to hydrolyze to formaldehyde and an amino alcohol. Preferably, the oxazolidine and hexahydro-1,3,5-triazine biocides hydrolyze to produce an amino alcohol having the following formula

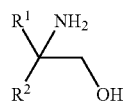

wherein $R^1$ is hydrogen, $C_1$-$C_4$ alkyl or hydroxymethyl and $R^2$ is hydrogen or $C_1$-$C_4$ alkyl. Preferably, $R^1$ is hydrogen, methyl, ethyl or hydroxymethyl. Preferably, $R^2$ is hydrogen, methyl or ethyl. For example, DMO hydrolyzes to produce formaldehyde and 2-amino-2-methylpropanol (AMP), as shown in the scheme below:

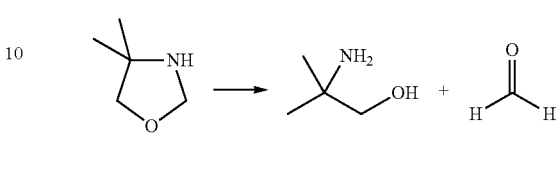

In the method of this invention, the aminoalcohol resulting from hydrolysis of the biocide is separated and measured. The molar amounts of aminoalcohol and formaldehyde are equal, so quantifying the aminoalcohol allows one to determine the level of formaldehyde.

A mixed-mode chromatographic column is one in which the stationary phase has both a long alkyl chain and a negatively charged groups. Preferably the negatively charged group is part of the long alkyl chain. Preferably, the long alkyl chain has at least eight carbon atoms, preferably at least ten, preferably at least twelve, preferably at least sixteen. Preferably, the alkyl chain is linear. Preferably, the negatively charged group is a sulfonic acid, a carboxylic acid or a salt of a sulfonic or carboxylic acid; preferably a sulfonic acid or salt thereof. The stationary phase comprises several polar ionizable groups with a pKa of approximately 1 in the interior of a hydrophobic chain. These groups are believed to attract enough water to keep the stationary phase in a wetted state with unfolded alkyl chains.

Preferably, the amino alcohol is detected using a charged aerosol detector.

Preferably, the biocide concentration is from 0.02% to 75%, preferably at least 0.03%, preferably at least 0.04%, preferably at least 0.05%, preferably at least 0.07%, preferably at least 0.1%, preferably at least 0.2%; preferably no more than 50%, preferably no more than 40%, preferably no more than 30%, preferably no more than 20%, preferably no more than 10%, preferably no more than 5%.

In the present method, an aqueous solution of a biocide is tested by dilution with water prior to chromatographic analysis. The concentration range of samples as prepared for analysis is 50 ppm-500 ppm.

EXAMPLES

The analytical parameters were as follows:
Flow Rate: 2 mL/min
Stop time: 12 mins
Solvent Composition:
Isocratic
A: 98% H20 w/0.1% TFA B: 0.2% Acetonitrile
Injection Volume: 15 uL
Column Temperature: 50° C. Column Type:PRIMESEP100 4.6 mm×150 mm

TABLE 1

The indirect determination of Formaldehyde (FA) based on the quantification of AMP in a 250 ppm DMO sample in Water.

FA Determined through Indirect Determination after Hydrolysis using bi-Products of DMO

|  | Active | RT | Area of AMP | ppm AMP | conversion | DF | ppm FA |
|---|---|---|---|---|---|---|---|
| Prep 1: Injection 1 | DMO | 5.17 | 117.5 | 91.16 | 0.000337 | 7 | 79.54 |
| Prep 1: Injection 2 |  | 5.17 | 115.6 | 89.68 |  |  | 78.25 |
| Prep 2: Injection 1 |  | 5.17 | 116.5 | 90.38 |  |  | 78.86 |
| Prep 2: Injection 2 |  | 5.17 | 115.7 | 89.76 |  |  | 78.32 |
|  |  |  |  |  |  | avg. | 78.74 |

TABLE 2

The indirect determination of Formaldehyde based on the quantification of a 250 ppm DMO sample in water.

FA Determined through Conversion of DMO

|  | Active | RT | Area of DMO | ppm DMO | conversion | DF | ppm FA |
|---|---|---|---|---|---|---|---|
| Prep 1: Injection 1 | DMO | 6.394 | 78 | 99.58 | 0.000297 | 7 | 76.58 |
| Prep 2: Injection 1 |  | 6.394 | 78.7 | 100.48 |  |  | 77.26 |
|  |  |  |  |  |  | avg. | 76.92 |

The data above prove that formaldehyde can be determined indirectly. When quantifying DMO and AMP, the determination of formaldehyde once converted back to parts per million should be equal ±5 ppm.

The following formulas were used to tabulate the conversions recorded above.

X ppm AMP=((1 mg/1000 mL)×(1 mol AMP/MW AMP (mg/mol))×volume Sample=mol AMP

X mol AMP×(1 mol FA/1 mol AMP)×(30030 mg/mol FA/1 mol FA)×dilution factor=mg FA mg FA×(1/original Volume of sample)×0.37 (% of FA)×1000 (to convert to ppm)=ppm FA

The invention claimed is:

1. A method for measuring formaldehyde in an aqueous solution of an oxazolidine or hexahydro-1,3,5-triazine biocide; said method comprising separating an amino alcohol produced by hydrolysis of said biocide via mixed mode chromatography and detecting said amino alcohol using a charged aerosol detector or an evaporative light scattering detector.

2. The method of claim 1 in which the oxazolidine or hexahydro-1,3,5-triazine biocide hydrolyzes to produce an amino alcohol having of formula

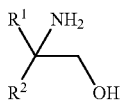

wherein $R^1$ is hydrogen, $C_1$-$C_4$ alkyl or hydroxymethyl and $R^2$ is hydrogen or $C_1$-$C_4$ alkyl.

3. The method of claim 2 in which the oxazolidine or hexahydro-1,3,5-triazine biocide is 4,4-dimethyloxazolidine, 5-ethyl-3,7-dioxa-1-azabicyclo[3,3,0]octane, N,N-methylenebis(5-methyloxazolidine), N,N,N-tris(2-hydroxyethyl)hexahydrotriazine or N,N,N-tris(2-hydroxypropyl) hexahydrotriazine.

4. The method of claim 3 in which a charged aerosol detector is used.

5. The method of claim 4 in which the mixed mode chromatography uses a stationary phase comprising an alkyl chain of least eight carbon atoms and a negatively charged group.

6. The method of claim 5 in which the negatively charged group is a sulfonic acid, a carboxylic acid or a salt of a sulfonic or carboxylic acid.

7. The method of claim 6 in which the oxazolidine or hexahydro-1,3,5-triazine biocide is 4,4-dimethyloxazolidine, 5-ethyl-3,7-dioxa-1-azabicyclo[3,3,0]octane or N,N-methylenebis(5-methyloxazolidine).

* * * * *